(12) United States Patent
Jackson

(10) Patent No.: US 7,678,042 B2
(45) Date of Patent: Mar. 16, 2010

(54) DEVICES AND METHODS FOR PROMOTING OR ENHANCING MALE ERECTILE FUNCTION

(76) Inventor: Thomas Jackson, 54401 Tahquitz Dr., P.O. Box 1726, Idyllwild, CA (US) 92549

( * ) Notice: Subject to any disclaimer, the term of this patent is extended or adjusted under 35 U.S.C. 154(b) by 1231 days.

(21) Appl. No.: 10/867,009

(22) Filed: Jun. 15, 2004

(65) Prior Publication Data

US 2005/0277907 A1 Dec. 15, 2005

(51) Int. Cl.
*A61F 5/00* (2006.01)
(52) U.S. Cl. .......................................................... 600/41
(58) Field of Classification Search ............. 600/38–41; 128/844
See application file for complete search history.

(56) References Cited

U.S. PATENT DOCUMENTS

| 2,581,114 | A | * | 1/1952 | Larson | 600/41 |
| 3,773,040 | A | * | 11/1973 | Gavrilovich | 600/41 |
| 5,027,800 | A | * | 7/1991 | Rowland | 600/39 |
| 5,370,130 | A | * | 12/1994 | Hess | 128/844 |
| 5,370,131 | A | * | 12/1994 | Hess | 128/844 |
| 5,386,992 | A | * | 2/1995 | Jaghab | 473/474 |
| 5,715,839 | A | * | 2/1998 | Strauss et al. | 128/842 |
| 5,799,657 | A | * | 9/1998 | Pasczuk et al. | 128/844 |
| D431,865 | S | * | 10/2000 | Norton et al. | D24/143 |

* cited by examiner

*Primary Examiner*—Samuel G Gilbert
(74) *Attorney, Agent, or Firm*—The Nath Law Group; Jerald L. Meyer

(57) ABSTRACT

A closed ringed structure having an arch segment embedded within is demonstrated for promoting and/or enhancing erectile function. It is for external placement on the shaft of a user's penis, including a closed, hollow tube of relatively elastic material forming a ring, the hollow tube completely encircles the shaft of a user's penis when placed on the user's penis, or completely encircles the shaft of the user's penis and the user's scrotum and testicles; and contains a filled arch segment within the hollow tube, for providing compression of the dorsal vein of the user's penis, where the outer diameter of the arch segment is of a smaller diameter than an outer diameter of the hollow tube.

61 Claims, 5 Drawing Sheets

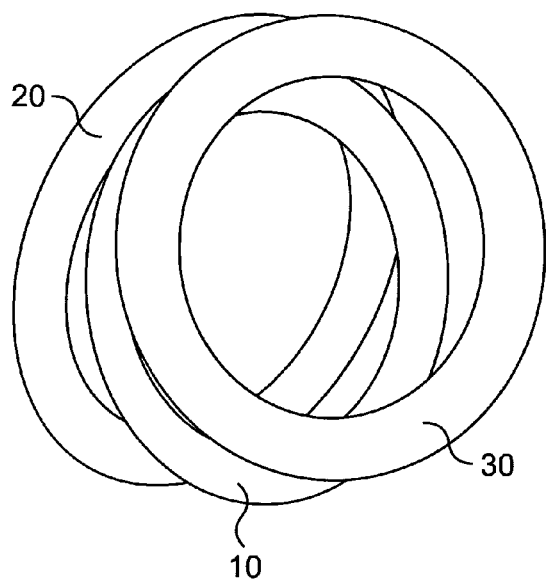
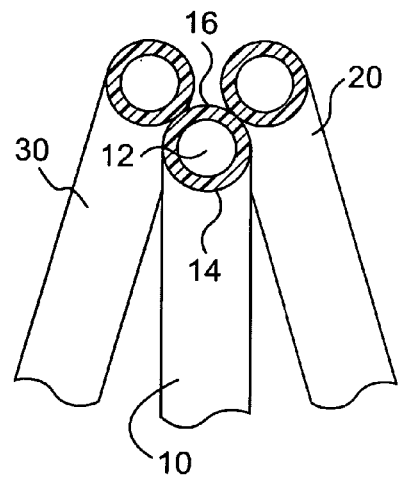
FIG. 4A  FIG. 4B
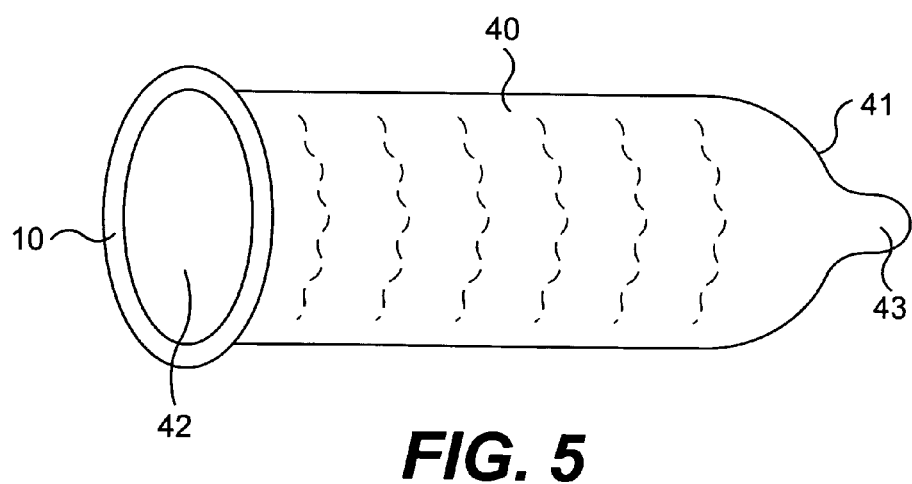
FIG. 5

DEVICES AND METHODS FOR PROMOTING OR ENHANCING MALE ERECTILE FUNCTION

BACKGROUND OF THE INVENTIVE SUBJECT MATTER

1. Field of the Inventive Subject Matter

The inventive subject matter relates to novel devices and methods for promoting or enhancing male erectile function, and for treating erectile dysfunction.

2. Background

More than 100 years ago, G. R. Phillips, M.D. wrote the following in the St. Louis Medical Era, 1895-1896: "With rare exceptions, it is the evident intent of nature that every adult male be accorded the pleasure, satisfaction and the power of performing the sexual act. When a condition exists that strips one of this right, be the condition a real or a fancied ill, we have resulting impotence. To acquire an erection is essential, to maintain the same for a time sufficient for the completion of the sexual act is equally so, that one may be potent." All fields of medical science advanced during the Victorian Age, and the study of the male penis became scientific. Early urologists laid down rules in an exact science for performing observations and testing the soundness of their conclusions. Their conclusions were that impotency does exist.

Now, more than 100 years later and with all the research done on this subject, millions of men around the world still suffer erectile dysfunction at some time in their lives.

Erectile dysfunction affects millions of men. It is estimated that the number of American men with erectile dysfunction ranges from 15 million to 30 million. Although for some men erectile function may not be the best or most important measure of sexual satisfaction, for many men erectile dysfunction creates mental stress that affects their interactions with family and associates. Many advances have occurred in both diagnosis and treatment of erectile dysfunction. However, its various aspects remain poorly understood by the general population and by most health care professionals. Lack of a simple definition, failure to delineate precisely the problem being assessed, and the absence of guidelines and parameters to determine assessment and treatment outcome and long-term results, have contributed to this state of affairs by producing misunderstanding, confusion, and ongoing concern.

Prior-art Treatments of erectile dysfunction. Erectile dysfunction can be treated, with variable degrees of success, by a variety of methods. Most physicians suggest that treatments proceed from least to most invasive. Cutting back on drugs with harmful side effects is considered first. For example, different drugs for high blood pressure work in different ways. Psychotherapy and behavior modifications in selected patients are considered next if indicated, followed by oral or locally injected drugs, vacuum devices, and surgically implanted devices. In rare cases, surgery involving veins or arteries may be considered.

Psychotherapy. Experts often treat psychologically based erectile dysfunction using techniques that decrease the anxiety associated with intercourse. The patient's partner can help with the techniques, which include gradual development of intimacy and stimulation. Such techniques also can help relieve anxiety when erectile dysfunction from physical causes is being treated.

Drug Therapy. Drugs for treating erectile dysfunction can be taken orally, injected directly into the penis, or inserted into the urethra at the tip of the penis. In March 1998, the Food and Drug Administration approved Viagra, the first pill to treat erectile dysfunction. Recently, the FDA granted approval for two additional oral medications, vardenafil hydrochloride (Levitra) in August 2003 and, most recently, Cialis (tadalafil) in November 2003.

Additional oral medicines are being tested for safety and effectiveness. Taken before sexual activity, Viagra, Levitra and Cialis work by enhancing the effects of nitric oxide, a chemical that relaxes smooth muscles in the penis during sexual stimulation and allows increased blood flow. While oral medicines improve the response to sexual stimulation they do have potential side effects and other limitations, such as delayed time of onset. Further, men who take nitrate-based drugs, such as nitroglycerin for heart problems, should not use any of these medications because the combination can produce a sudden drop in blood pressure. In addition, none of these medications should be taken with any of the drugs called alpha-blockers, which are used to treat prostate enlargement or high blood pressure.

Oral testosterone can reduce erectile dysfunction in some men with low levels of natural testosterone, but it is often ineffective and may produce liver damage. Patients also have claimed that other oral drugs—including yohimbine hydrochloride, dopamine and serotonin agonists, and trazodone—are effective, but the results of scientific studies to substantiate these claims have been inconsistent. Improvements observed following use of these drugs may be examples of the placebo effect.

Many men achieve stronger erections by injecting drugs into the penis, causing it to become engorged with blood. Drugs such as papaverine hydrochloride, phentolamine, and alprostadil widen blood vessels. However, along with the inconvenience of injections, such drugs may create unwanted side effects, including persistent erection and scarring.

A system for inserting a pellet of alprostadil into the urethra is also currently available. The system uses a prefilled applicator to deliver the pellet about an inch deep into the urethra. An erection will begin within 8 to 10 minutes and may last 30 to 60 minutes. The most common side effects are aching in the penis, testicles, and area between the penis and rectum; warmth or burning sensation in the urethra; redness from increased blood flow to the penis; and minor urethral bleeding or spotting.

Constriction and Vacuum/Constriction Devices. Mechanical vacuum/constriction devices produce erection by creating a partial vacuum around the penis, which draws blood into the penile corpora cavernosa, engorging and expanding the penis. The devices have three components: (a) a plastic cylinder, which covers the penis; (b) a pump, which draws air out of the cylinder; and (c) an elastic ring, which, when fitted over the base of the penis, traps the blood and sustains the erection after the cylinder is removed and during sexual activity. One variation of the vacuum/constriction device involves a semi-rigid rubber sheath that is placed on the penis and remains there after erection is attained and during intercourse.

Vacuum/constriction devices are at times effective at generating and maintaining erections in some patients with erectile dysfunction. However, as with intracavernosal injection therapy, there is a significant rate of patient dropout with these devices: the devices are difficult for many patients to use, and this is especially so in those with impaired manual dexterity. Also, vacuum/constriction devices may impair ejaculation, which then produces patient discomfort. Patients and their partners often are bothered by the lack of spontaneity in sexual relations that may occur with this procedure. The patient is at times also bothered by the general discomfort that can occur while using vacuum/constriction devices. Further complicating their use, partner involvement in training with vacuum/constriction devices is often important for successful outcome, especially in regard to establishing a mutually satisfying level of sexual activity.

Constriction devices are known in the art. Representative U.S. Patents to penile constriction devices include the following:

U.S. Pat. No. 5,295,946 issued Mar. 22, 1994 to Collins, discloses a device for affecting or enhancing erection of the penis, comprising an external inflatable cuff which encircles the shaft of the penis at its base and extends distally. The cuff is provided with a plurality of volume expandable annular spaces arranged parallel to one another. The spaces are filled with fluid under pressure from a squeeze bulb to affect a tourniquet action. The spaces are inflated sequentially in a proximal to distal direction.

U.S. Pat. No. 5,306,227 issued Apr. 26, 1994 to Osbon, et al., discloses an integral cincture band of elastic material which includes a pair of semi-ellipsoidal handles and an enlarged region to be aligned with the urethra of the user's male sex organ so as to relatively reduce the urethral constriction for improved seminal fluid discharge. Radially inwardly projecting regions of predetermined radius of curvature which is relatively large to the overall ring are provided in predetermined circumferential locations on each lateral side of the dorsal centerline. Relatively inelastic material, such as spherical elements of hardened plastic, may be included in the inwardly projecting regions to further enhance specific circumferentially located blood flow restriction pressures.

U.S. Pat. No. 5,327,910 issued Jul. 12, 1994 to Flynn, discloses a therapeutic device for the treatment of male sexual dysfunction, which has first and second substantially rigid portions interconnected by malleable or deformable portions. The device is fitted to the base of the male penis and by selective deformation of the device, the first portion constricts blood flow through the penile veins to enable the user to achieve a penile erection; the second portion constricts the urethra to prevent premature ejaculation; and the malleable or deformable portions constrict blood flow through the penile arteries to overcome Priapism. The device has a core, e.g. of copper wire, within a deformable resilient sheath, with grooves or slots which allow blood flow through the blood vessels under the skin of the penis when in use.

U.S. Pat. Nos. 5,421,324 and 5,526,803 issued Jun. 6, 1995 and Jun. 18, 1996, respectively, to Kelly, disclose a male truss for assisting in producing and maintaining an erection. A linear rigid member is mounted upon a loop capable of drawing the member into biasing contact against the dorsal side of the penis to restrict the flow of blood moving through the dorsal vein.

U.S. Pat. No. 5,439,007 issued Aug. 8, 1995 to Fischer, discloses a suspensory for improving the erection of the human male penis by means of deliberately choking the backflow of the venous blood, including a rigid, generally rectangular ring composed of two crossbars and two sidebars, which, in use, surrounds the penis as well as the scrotum, and which carries one rounded bulge at the center of its upper crossbar that presses on the topside of the penis near the abdomen, and one bulge on or adjacent its lower bar that presses on the root of the penis at the backside of the scrotum. These two bulges are shaped and placed such as to choke all three main veins, the vena dorsalis superficialis and the vena dorsalis profunda penis at the topside of the penis, and the venae profundae penis at the underside of the penis behind the scrotum, such that the arteries and nerve cords of the penis that run parallel to those choked veins are crowded sideways by said bulges into the empty corners of the rectangular ring so that arteries and nerve cords remain essentially unchoked. The lower bulge may be provided on a rearward extension rod which carries a rectal cone.

U.S. Pat. No. 5,695,444 issued Dec. 9, 1997 to Chaney, discloses an elastic ring for assisting a male to obtain and maintain an erection, having two prongs circumferentially spaced apart and extending from the inside diameter of the ring inwardly of the ring opening and has a protuberance formed on the inside of ring substantially diametrically opposite of the prongs. The device encircles the penis and scrotum so as to apply a compressive force rearwardly of the root of the penis so that the external conspicuous part of the penis and the more concealed root part can become rigidified or erect and involved in the sexual act.

U.S. Pat. No. 5,997,469 issued Dec. 7, 1999 to Northcutt, discloses a sexual aid device that encircles the base of the penis. The device may be constructed as a single ring, or as a set of rings that can be used together in various conformations. The device includes a size adjustment means that allows the user to vary the size of the central through hole so that a user of the device is always ensured of a proper fit. The device may also include an extension means to directly stimulate the female's clitoral region. Alternatively, the device may be formed with an oval shape as opposed to a round shape to achieve the objective of direct stimulation of the clitoris.

U.S. Pat. No. 6,319,194 issued Nov. 20, 2001 to Wulf, discloses a penis erection stabilizer adapted for mounting on the base of a male penis. The stabilizer includes an outer ring, a concentric smaller inner ring and a latex sheath. The latex sheath connects the two rings. The outer ring and smaller inner ring are also made of latex. One end of the sheath is attached to an inner circumference of the outer ring. An opposite end of the sheath is attached to an inner circumference of the inner ring. In operation, the outer and inner ring are stretched over the head of the penis and along the length of the penis. The smaller inner ring is then placed next to the base of the penis and next to the torso with the outer ring disposed around the inner ring. The inner ring with added pressure from the outer ring provide a necessary pressure to contain the blood supply in the penis, thus helping insure a natural erection. Also, the inner ring can be unrolled from a portion of the sheath for placing the inner ring next to the upper ring.

These prior art patents do not describe the novel and improved inventive subject matter claimed herein.

Surgery. Surgery for treating erectile dysfunction usually has one of three goals:

1. to reconstruct arteries to increase flow of blood to the penis;
2. to block off veins that allow blood to leak from the penile tissues; or
3. to implant a penile prosthesis device that can allow the penis to become erect.

Surgery to repair arteries can reduce erectile dysfunction caused by obstructions that block the flow of blood. The best candidates for such surgery are young men with discrete blockage of an artery because of an injury to the crotch or fracture of the pelvis. However, the procedure is not widely used, as it is almost never successful in older men with widespread arterial blockage.

Surgery to veins that allow blood to leave the penis usually involves an opposite procedure—intentional blockage. In theory, blocking off veins can reduce the leakage of blood that diminishes the rigidity of the penis during erection. However, experts have raised questions about the long-term effectiveness of ligation, and it is rarely used.

Implanted devices, known as prostheses, can restore the ability to achieve erection in many men with erectile dysfunction. Various forms of penile prostheses are available for patients who fail with, or refuse, other forms of therapy; essentially, there are two basic designs: rigid or semi-rigid, and inflatable.

Rigid, malleable, and semirigid penile prostheses consist of specially constructed rods, generally plastic or silicone rubber, which are placed inside the corpora cavernosa of the penis. Such devices are implanted via an incision made on the underside the penis, and one rod is inserted in each corpora cavernosa. The procedure is an ambulatory, out patient procedure. It is particularly useful for the elderly and those with reduced strength of hands because its use requires no special manipulation. The user manually adjusts the position of the penis and, therefore, the rods. Adjustment does not affect the width or length of the penis.

Inflatable implants consist of paired cylinders, which are surgically inserted inside the penis and can be expanded using pressurized fluid. Tubes connect the cylinders to a fluid reservoir and a pump, which are also surgically implanted. The patient inflates the cylinders by pressing on the small pump, located under the skin in the scrotum. Inflatable implants can expand the length and width of the penis somewhat. They also leave the penis in a more natural state when not inflated. With an inflatable implant, erection is produced by squeezing a small pump implanted in a scrotum. The pump produces fluid to flow from a reservoir residing in the lower pelvis to cylinders residing in the penis. The cylinders expand to create the erection.

The effectiveness, complications, and acceptability vary among the types of prostheses, with the main problems being mechanical failure, infection, and erosions. Silicone particle shedding has been reported, including migration to regional lymph nodes. There is also a risk of the need for subsequent operation(s) with all mechanical devices. Although the inflatable prostheses may yield a more physiologically natural appearance, they have had a higher rate of failure requiring reoperation. Men with diabetes mellitus, spinal cord injuries, or urinary tract infections have an increased risk of prosthesis-associated infection. This form of treatment is considered to be inappropriate in patients with severe penile corporal fibrosis, or severe medical illness. Circumcision may also be required for patients with phimosis and balanitis.

Technologies in Development. Advances in implants, suppositories, injectable medications, and vacuum devices have expanded the options for men seeking treatment for erectile dysfunction. These advances have also helped increase the number of men seeking treatment. Gene therapy for erectile dysfunction is now being tested in several centers and may offer a long-lasting therapeutic approach for select causes of erectile dysfunction involving genetic deficiencies.

The National Institute of Diabetes and Digestive and Kidney Diseases ("NIDDK") sponsors programs aimed at understanding the causes of erectile dysfunction and finding treatments to reverse its effects. NIDDK's Division of Kidney, Urologic, and Hematologic Diseases supported the researchers who developed Viagra and continue to support basic research into the mechanisms of erection and the diseases that impair normal function at the cellular and molecular levels, including diabetes and high blood pressure.

Despite increasing emphasis on eliminating the stigma that some perceive as surrounding erectile dysfunction, and increasing emphasis on actively treating erectile dysfunction using the methods and devices described above, there remains a significant need for novel and improved devices and methods for promoting or enhancing male erectile function, and for treating erectile dysfunction. Most particularly, there is a great need for comparatively simple, inexpensive, and non-invasive devices and methods of first resort which can be used by persons suffering from erectile dysfunction.

The inventive subject matter satisfies this need by providing novel devices and methods for promoting or enhancing male erectile function, and for treating erectile dysfunction. Advantages of the inventive subject matter over the prior art include:

Safety. In general, the FDA recommends that devices which constrict the user's penis be worn for no longer than 45 minutes at a time. The inventive devices can be safely worn for at least the maximum time recommended by the FDA.

Effectiveness. As discussed in detail herein, the inventive devices are at least as effective as any constrictive device.

Convenience. The inventive devices are simple to use, washable, and are expected to be easily replaceable if damaged.

Comfort. The inventive devices are as comfortable to use as "novelty" penis rings while providing a therapeutic benefit, and are significantly more comfortable than prior art constrictive devices having wire, metal, and hard plastic parts.

Partner Acceptance. The inventive devices are unobtrusive in use and may bring additional pleasure to the user's sexual partner. Further, the inventive devices are simple and quick to apply to the user's penis, promoting spontaneity in initiating sexual activity and avoiding distraction during sexual activity.

It is expected that the inventive devices and methods will be most beneficial to patients having reversible causes of erectile dysfunction, such as:

1. Patients on medications for high blood pressure;
2. Patients on medicines for depression;
3. Patients who have endocrine problems, such thyroid or pituitary problems;
4. Patients who have partner conflict;
5. Patients who smoke cigarettes;
6. Patients who use recreational drugs such as alcohol, methamphetamine, cocaine, and heroin;
7. Patients who have an anatomical abnormality of the penis; and
8. Patients with a correctable cause of vascular impotence.

However, the inventive devices may be utilized by any man for promoting or enhancing erectile function, including specifically those men who have no perceived or diagnosed erectile dysfunction, yet wish to have firmer, longer-lasting erections more often or more consistently.

SUMMARY OF THE INVENTIVE SUBJECT MATTER

The present inventive subject matter relates to a device for external placement on the shaft of a user's penis, for promoting or enhancing male erectile function, comprising:

(i) a closed, hollow tube of relatively elastic material forming a ring, said hollow tube completely encircling the shaft of a user's penis when placed on said user's penis, or completely encircling the shaft of said user's penis and said user's scrotum and testicles; and (ii) a filled arch segment within said hollow tube, for providing compression of a dorsal vein of said user's penis.

The inventive subject matter further relates to a device for external placement on the shaft of a user's penis, for promoting or enhancing male erectile function, comprising:

(i) a first closed, hollow tube of relatively elastic material forming a ring, said hollow tube completely encircling the shaft of a user's penis when placed on said user's penis; and (ii) a second closed, hollow tube of relatively elastic material forming a ring, said hollow tube completely encircling the shaft of a user's penis when placed on said user's penis, or completely encircling the shaft of said user's penis and said user's scrotum and testicles, wherein said first ring has an inner surface proximal to said penile shaft and an outer surface distal to said penile shaft, and wherein said second ring is connected to said outer surface of said first ring.

In addition, the inventive subject matter relates to a method for promoting or enhancing male erectile function, comprising:

(a) providing a device for providing compression of a dorsal vein of a user's penis which is sufficient to promote arterial blood inflow in excess of venous blood outflow from said user's penis, comprising:

(i) a first closed, hollow tube of relatively elastic material forming a first ring, said hollow tube completely encircling the shaft of said user's penis when placed on said user's penis, or completely encircling the shaft of said user's penis and said user's scrotum and testicles, and (ii) a filled arch segment within said hollow tube; and (b) placing said device so as to encircle said user's penis with said filled arch segment located on the dorsal surface of said user's penis.

Further, the inventive subject matter relates to a method for promoting or enhancing male erectile function and promoting responsible sexual practices, comprising:

(a) applying a condom, having a closed distal end and an open proximal end, to said user's penis;

(b) providing a device comprising:

(i) a closed, hollow tube of relatively elastic material forming a ring, said hollow tube completely encircling the shaft of a user's penis when placed on said user's penis, or completely encircling the shaft of said user's penis and said user's scrotum and testicles, and (ii) a filled arch segment within said hollow tube; and (c) placing said device so as to encircle the base of said user's penis and entrap the open proximal end of said condom, with said filled arch segment located on the dorsal surface of said user's penis.

Additionally, the inventive subject matter relates to a method for treating erectile dysfunction in a patient in need thereof, comprising:

(a) providing a device for providing compression of a dorsal vein of a user's penis which is sufficient to promote arterial blood inflow in excess of venous blood outflow from said user's penis, comprising:

(i) a first closed, hollow tube of relatively elastic material forming a first ring, said hollow tube completely encircling the shaft of said user's penis when placed on said user's penis, or completely encircling the shaft of said user's penis and said user's scrotum and testicles, and (ii) a filled arch segment within said hollow tube; and (b) placing said device so as to encircle said user's penis with said filled arch segment located on the dorsal surface of said user's penis.

BRIEF DESCRIPTION OF THE DRAWINGS

FIG. 4A is a drawing which depicts a connected triple-ring embodiment of the inventive subject matter.

FIG. 4B is a drawing which depicts a sectional view of a connected triple-ring embodiment of the inventive subject matter, depicting the connection of the three rings.

FIG. 5 is a drawing which depicts a single-ring embodiment of the inventive subject matter, having an exemplary reservoir-tip condom which is attached to or integrally formed with said ring.

DETAILED DESCRIPTION OF THE INVENTIVE SUBJECT MATTER

Definitions

Figure 1A:
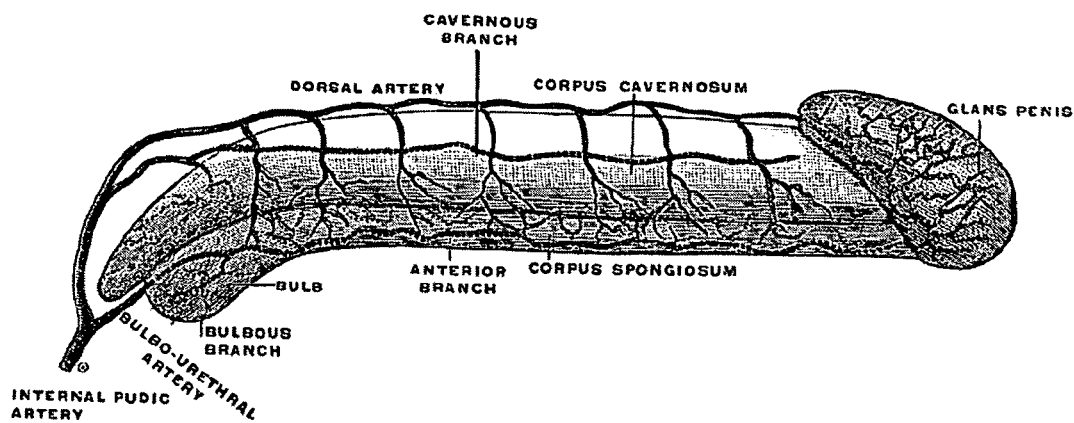
FIG. 1A is a drawing which depicts the arterial physiology of the human male penis.

The term "promoting" the biological activity, function, health, or condition of an organism as used herein refers to process of forwarding, furthering, encouraging, advancing, or contributing to the growth, enlargement, or prosperity of the activity, function, health, or condition.

The term "enhancing" the biological activity, function, health, or condition of an organism refers to the process of augmenting, fortifying, strengthening, or improving.

The term "elastic" as used herein refers to the property of a material which is capable of resuming its original shape after bending, stretching, twisting, or compression.

The term "erectile dysfunction" as used herein refers to a condition in which a male patient experiences a total inability to achieve erection, an inconsistent ability to do so, or a tendency to sustain only brief erections.

The term "patient" as used herein refers broadly to an individual subject who receives care, whether medical or otherwise, to promote or enhance an activity, function, health, or condition.

The term "ring" as used herein refers to the solid generated by the revolution of a circle, or other generally circular figure, about an axis lying in the same plane as the circular figure.

The Inventive Subject Matter

The present inventive subject matter relates generally to devices and methods, for promoting or enhancing male erectile function and for treating erectile dysfunction.

In 1992, the National Institutes of Health Consensus Development Conference on Impotence found that:

(1) the likelihood of erectile dysfunction increases with age but is not an inevitable consequence of aging;

(2) embarrassment of patients and reluctance of both patients and health care providers to discuss sexual matters candidly contribute to underdiagnosis of erectile dysfunction;

(3) many cases of erectile dysfunction can be successfully managed with appropriately selected therapy;

(4) the diagnosis and treatment of erectile dysfunction must be specific and responsive to the individual patient's needs and that compliance as well as the desires and expectations of both the patient and partner are important considerations in selecting appropriate therapy; and (5) erectile dysfunction is an important public health problem deserving of increased support for basic science investigation and applied research.

The term "impotence" has in the past been used to signify the inability of the male to attain and maintain erection of the penis sufficient to permit satisfactory sexual intercourse. However, this use has often led to confusing and uninterpretable results in both clinical and basic science investigations. This, together with its pejorative implications, suggests that the more precise term "erectile dysfunction" be used instead to signify an inability of the male to achieve an erect penis as part of the overall multifaceted process of male sexual function.

Erectile dysfunction can be a total inability to achieve erection, an inconsistent ability to do so, or a tendency to sustain only brief erections. These variations have made even defining erectile dysfunction and estimating its incidence difficult. However, estimates of the number of American men with erectile dysfunction ranges from 15 million to 30 million, depending on the criteria used.

According to the National Ambulatory Medical Care Survey, for every 1000 men in the United States, 7.7 physician office visits were made for erectile dysfunction in 1985. By 1999, that rate had nearly tripled to 22.3. The increase happened gradually, presumably as treatments such as vacuum devices and injectable drugs became more widely available, and discussing erectile function became accepted. Perhaps the most publicized advance to date has been the introduction of the oral drug sildenafil citrate, commonly known as Viagra, in March 1998.

Erectile dysfunction is often assumed to be a natural concomitant of the aging process, to be tolerated along with other conditions associated with aging. This assumption may not be entirely correct. For the elderly and for others, erectile dysfunction may occur as a consequence of specific illnesses or of medical treatment for certain illnesses, resulting in fear, loss of image and self-confidence, and depression.

Particularly in older men, erectile dysfunction often has a physical cause, such as disease, injury, or side effects of drugs. Any disorder that causes injury to the nerves or impairs blood flow in the penis has the potential to produce erectile dysfunction. Incidence increases with age: About 5 percent of 40-year-old men and between 15 and 25 percent of 65-year-old men experience erectile dysfunction. But it is not an inevitable part of aging. Erectile dysfunction is treatable at any age, and awareness of this fact has been growing. More men have been seeking help and returning to normal sexual activity because of improved, successful treatments for erectile dysfunction.

Figure 1B:
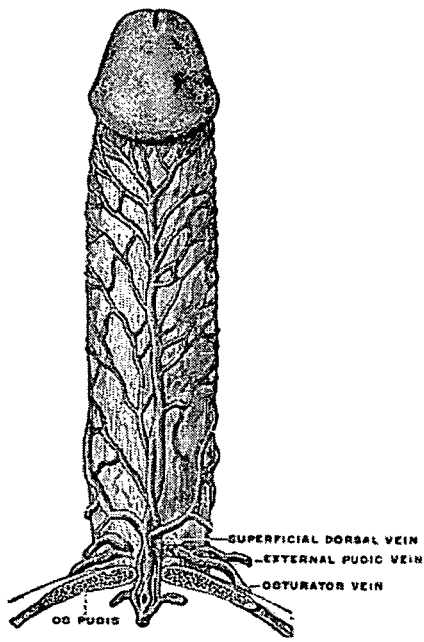
FIG. 1B is a drawing which depicts the venous physiology of the human male penis.
Figure 1C:
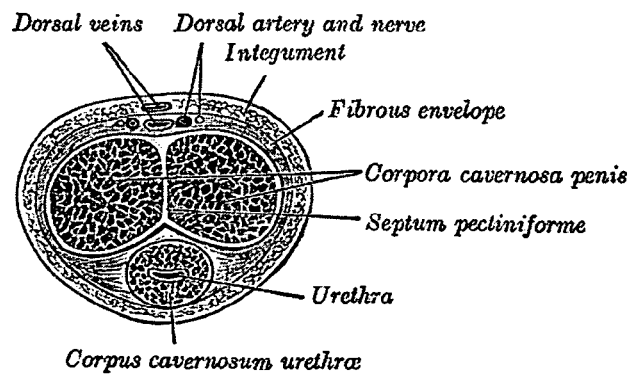
FIG. 1C is a drawing which depicts a transverse cross section of the internal physiology of the human male penis.
Figure 2:
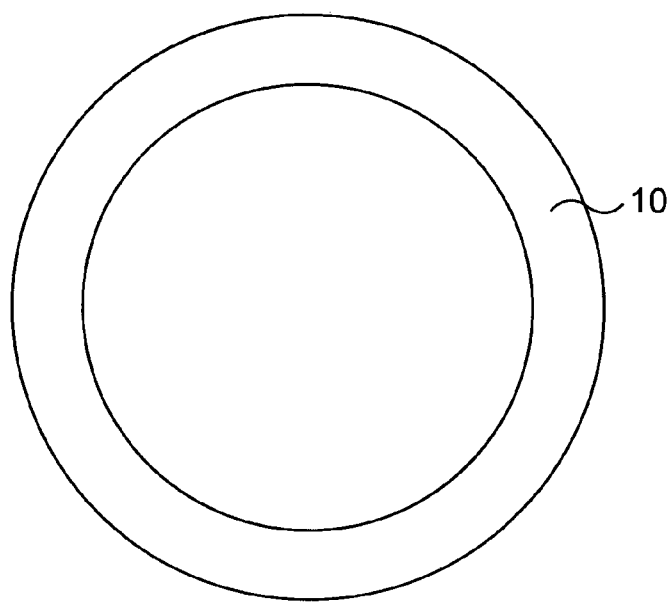
FIG. 2 is a drawing which depicts a single-ring embodiment of the inventive subject matter.
Figure 3A:
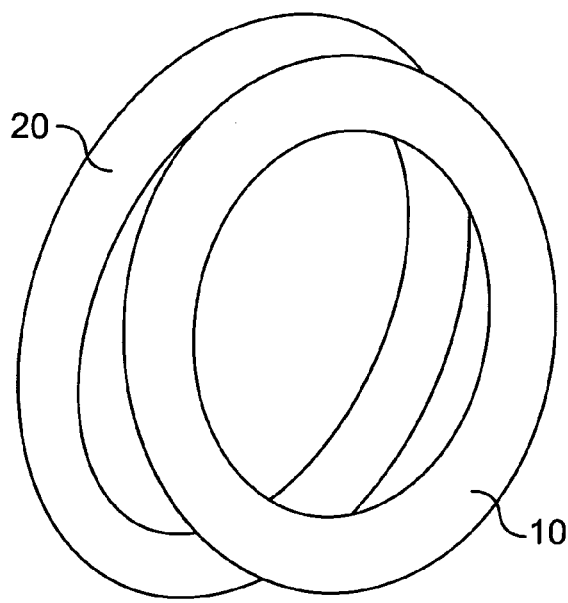
FIG. 3A is a drawing which depicts a connected double-ring embodiment of the inventive subject matter.
Figure 3B:
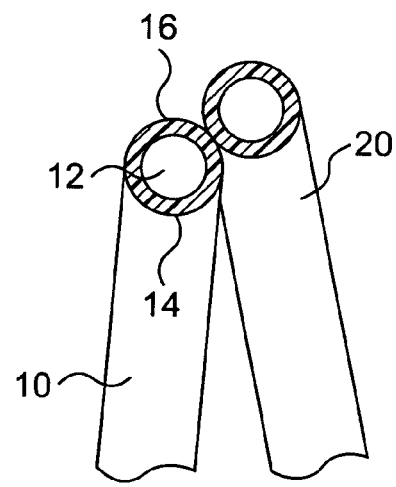
FIG. 3B is a drawing which depicts a sectional view of a connected double-ring embodiment of the inventive subject matter, depicting the connection of the two rings.
Figure 6:
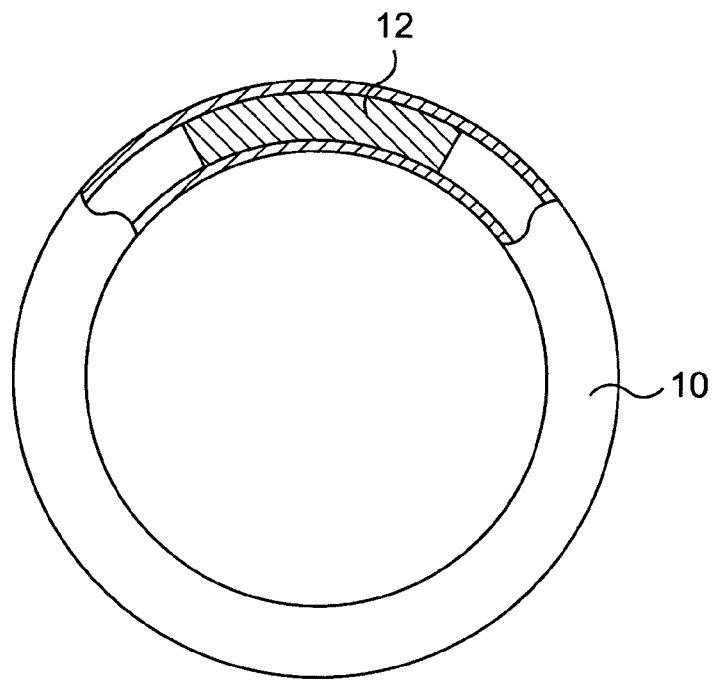
FIG. 6 is a drawing which depicts a cutaway view of a ring having a filled arch segment, as an embodiment of the inventive subject matter.
Figure 7:
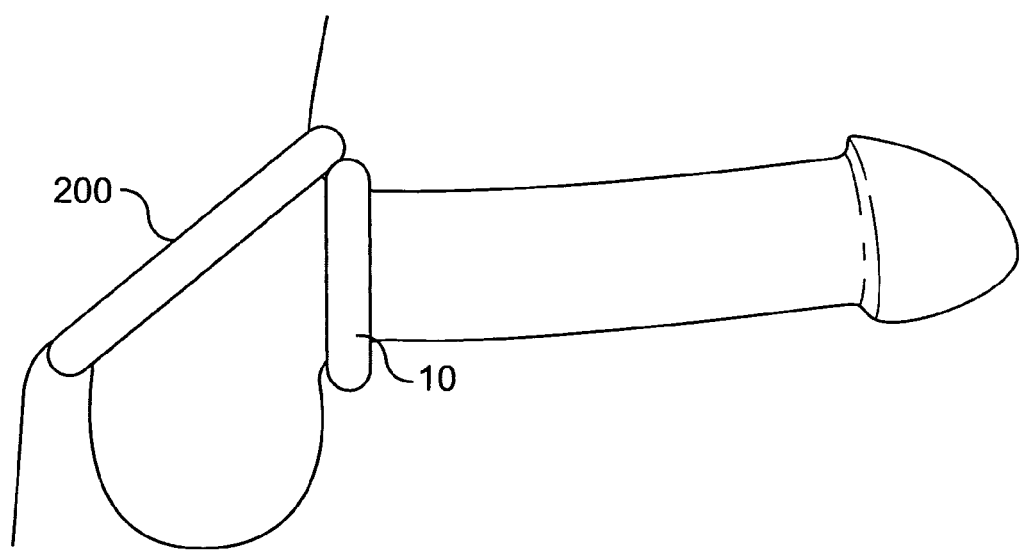
FIG. 7 is a drawing which depicts an in-use view of a double-ring embodiment of the inventive subject matter, with one ring sized to encircle the shaft of the user's penis, and a second ring sized to encircle the shaft of the user's penis and said user's scrotum and testicles.
Figure 8:
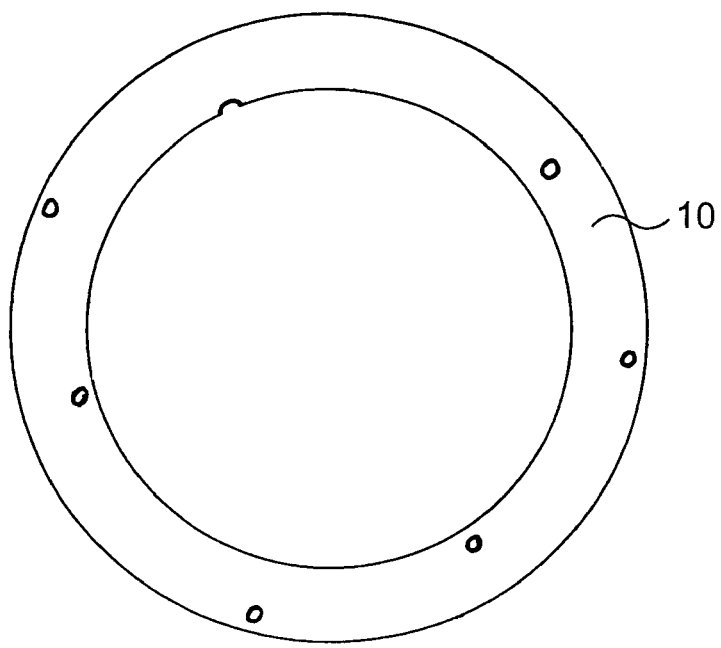
FIG. 8 is a drawing which depicts the embodiment of FIG. 2 with perforations.
Figure 9:
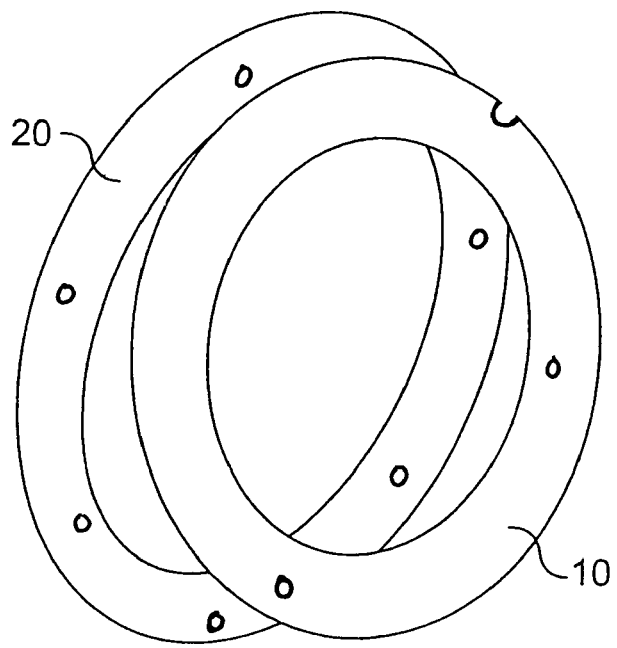
FIG. 9 is a drawing which depicts the embodiment of FIG. 3A with perforations.

A. Physiology of an Erection. As shown in FIG. 1, the interior of the penis contains three cylindrical-shaped vascular tissue structures, two corpora cavernosa, which run the length of the organ and which are responsible for erection and rigidity, and the corpus spongiosum. The urethra, the channel for urine and ejaculate, runs along the underside of the corpora cavernosa and is surrounded by the corpus spongiosum.

The corpora cavernosa are surrounded by a membrane, called the tunica albuginea, and contain a maze of blood vessels shaped as cavernous, spongelike spaces. Additional physiological structures in the penis include erectile tissue surrounding the urethra; two main arteries, the cavernosal arteries found in the center of each corporeal body; and several veins and nerves. The longest part of the penis is the shaft, at the end of which is the head, or glans penis. The opening at the tip of the glans, which allows for urination and ejaculation, is the meatus.

The physiological process of erection begins in the brain and involves the nervous and vascular systems. Neurotransmitters in the brain, such as epinephrine, acetylcholine, and nitric oxide, are some of the chemicals that initiate an erection. During sexual arousal, physical or psychological stimulation produces nerve signals which are transmitted through the spinal cord and subsequently through peripheral nerves, activating the vascular system to increase arterial blood flow to the penis and filling the corpora cavernosa with blood. Two arteries in the penis supply blood to erectile tissue and the corpora cavernosa, which become engorged and expand as a result of increased blood flow and pressure.

Because blood must stay in the penis to maintain rigidity, erectile tissue is enclosed by fibrous elastic sheathes called tunicae, which prevent blood from leaving the penis during erection. As the corpora cavernosa fill with blood, they expand and exert pressure against the veins that normally drain blood from the penis. This pressure constricts these veins, trapping blood in the penis. With more blood flowing in and less blood flowing out, the penis hardens, producing an erection.

Flaccidity occurs when the corpora cavernosa become constricted and empty. When muscles in the penis contract to stop the inflow of blood and open outflow channels, erection is reversed. Thus, when stimulation ends, or following ejaculation, pressure in the penis decreases, blood is released, and the penis resumes its normal shape. After a man climaxes, the erection often subsides quickly, and the penis becomes flaccid again.

B. Causes of erectile dysfunction. Causes contributing to erectile dysfunction can be broadly classified into two categories: organic and psychologic. In reality, while the majority of patients with erectile dysfunction are thought to demonstrate an organic component, psychological aspects of self-confidence, anxiety, and partner communication and conflict are often also important contributing factors.

Since an erection requires a precise sequence of events, erectile dysfunction can occur when any of the events is disrupted. The sequence includes nerve impulses in the brain, spinal column, and area around the penis; and response in muscles, fibrous tissues, veins, and arteries in and near the corpora cavernosa.

Damage to nerves, arteries, smooth muscles, and fibrous tissues, often as a result of disease, is the most common cause of erectile dysfunction. Diseases—such as diabetes, kidney disease, chronic alcoholism, multiple sclerosis, atherosclerosis, vascular disease, and neurologic disease—account for about 70 percent of erectile dysfunction cases. Between 35 and 50 percent of men with diabetes experience erectile dysfunction. The causes of erectile dysfunction are summarized below, and several of the most common caused are discussed in detail thereafter.

Endocrine Causes

1. Diabetes Mellitus (most common); erectile dysfunction occurs in 50% of men with Diabetes Mellitus 2. Abnormal glucose tolerance in 15% men with erectile dysfunction
3. Hypogonadism (5% of erectile dysfunction cases)
4. Hyperprolactinemia (Prolactinoma)
5. Hypothyroidism (6% of erectile dysfunction cases)
6. Hyperthyroidism
7. Cushing's Syndrome Vascular Causes
1. Peripheral Vascular Disease
2. Chronic Renal Failure Neurologic Causes
1. Multiple Sclerosis
2. Alzheimer's Disease
3. Parkinson's Disease
4. Spinal Cord Injury (50% erectile dysfunction risk)
5. Pelvic irradiation
6. Pelvic Surgery
7. Simple Prostatectomy: 10% erectile dysfunction risk
8. Radical Prostatectomy: 40% erectile dysfunction risk Habit Related Causes
1. Substance Abuse
2. Alcoholism (associated with Hypogonadism)
3. Anabolic steroids
4. Heroin
5. Methamphetamine
6. Tobacco Abuse; penile artery clot in 72% of men with 20 pack years of smoking Medications
1. A long list of prescription and over-the-counter medications, and illegal drugs, are known to produce erectile dysfunction as a side effect, as discussed in detail below.

Miscellaneous Causes
1. Obesity
2. Peyronie's Disease
3. Psychogenic causes (20% of erectile dysfunction cases)

Generally, the physical causes of erectile dysfunction can be grouped into three basic deficiencies:

1. Not enough blood flows into the penis. Many conditions can reduce blood flow into the penis, causing erectile dysfunction. The most common problem is atherosclerosis, or hardening of the arteries. Erectile dysfunction is often the first sign of this serious disease, which can lead to heart attacks and stroke. Diabetes, high blood pressure, high blood cholesterol, and cigarette smoking can produce atherosclerosis, and erectile dysfunction.

2. The penis cannot store blood during an erection. A man with this problem, called venous leak, typically cannot maintain an erection because blood does not remain trapped in the penis. Venous leak may result from smooth muscle damage in the penis.

3. Nerve messages from the brain or spinal cord do not reach the penis. If nerve stimuli do not reach the penis, an erection problem may occur. Some diseases can produce this problem, including diabetes, multiple sclerosis, and Parkinson's disease. Injuries or surgery to the genitals or pelvic area also can damage the penile nerves.

Diabetes. Diabetes is one of the most common causes of erectile dysfunction, and erectile dysfunction is common in diabetics. Diabetes can damage both the nerve and blood supply to the penis. Erectile dysfunction may be the first sign of diabetes or it can develop years after diagnosis. There are 9 million diabetic adult men in the U.S. and it is estimated that half are impotent and the other half will become impotent in time. More than half of men with diabetes develop erectile dysfunction within 10 years of diagnosis. The process involves premature and unusually severe hardening of the arteries. Peripheral neuropathy, with involvement of the nerves controlling erections, is seen commonly in diabetics. Fortunately, most men with erectile dysfunction resulting from diabetes respond to erectile dysfunction treatment options.

Neurologic Causes of Erectile Dysfunction. There are many neurological causes of erectile dysfunction. Diabetes, chronic alcoholism, multiple sclerosis, heavy metal poisoning, spinal cord and nerve injuries, and nerve damage from pelvic operations such as prostatectomy can produce erectile dysfunction.

For example, many men with diabetes mellitus may develop erectile dysfunction during their young and middle adult years. Physicians, diabetes educators, and patients and their families are sometimes unaware of this potential complication. Whatever the causal factors, discomfort of patients and health care providers in discussing sexual issues becomes a barrier to pursuing treatment.

Vascular Causes. The controllable risk factors for arteriosclerosis—overweight, lack of exercise, high cholesterol, cigarette smoking and high blood pressure—produce erectile failure often before progressing to affect the heart. The coronary arteries are 1.5-2.0 mm in diameter; the penile arteries are 0.6-0.7 mm in diameter, about one third the size of the coronary arteries, and can become obstructed sooner. Unless there is a change in lifestyle, coronary artery disease may follow vascular-related erectile dysfunction within a few years.

Surgical Causes. Surgery, especially radical prostate and bladder surgery for cancer, can injure nerves and arteries near the penis, causing erectile dysfunction. Injury to the penis, spinal cord, prostate, bladder, and pelvis can lead to erectile dysfunction by harming nerves, smooth muscles, arteries, and fibrous tissues of the corpora cavernosa.

Organic Erectile Dysfunction. By far, the most common cause of organic erectile dysfunction, especially in older men, involves the penile arteries, the penile veins, or both. When the problem is arterial, arteriosclerosis or hardening of the arteries is the usual culprit. Blunt trauma, sometimes from sports injuries, is a less frequent cause.

Venous Leak. Many experts believe that venous leak, or veno-occlusive incompetence, is the single most common vascular problem, especially in younger men. In a normal man during sexual excitement, arterial inflow increases 5-8 fold, and the venous blood outflow decreases dramatically, thus sustaining erection. When venous outflow controls fail to hold the blood in the penis, the erection becomes soft and may fail. Further, in those men born with a congenital venous leak, the venous drainage system in the penis does not diminish blood outflow properly during arousal. Many men in this group have never had a really hard erection. If a small venous leak is present during the patient's teens and twenties, his erections are virtually normal. As long as his arteries remain flexible, satisfactory erections can be achieved. Particularly as age progressively hardens and narrows the arteries, the blood inflow gradually diminishes, and the venous leak often then becomes apparent.

Men Treated for Prostate Cancer. Men who have been treated for prostate cancer with radiation therapy or a type of surgery called radical prostatectomy often develop erectile dysfunction as a side effect of treatment. These men also can often benefit from treatments for erectile dysfunction.

Drug-Induced Erectile Dysfunction. A great variety of prescription drugs such as blood pressure medications, anti-anxiety and anti-depressant drugs, glaucoma eye drops, and cancer chemotherapy agents are some of the many drugs associated with erectile dysfunction. In addition, many common over-the-counter drugs-for example antihistamines, appetite suppressants, and cimetidine—can produce erectile dysfunction as a side effect. Illicit drugs, such as methamphetamine, cocaine, and heroin, also are well-known causes of erectile dysfunction.

Psychological Factors for Erectile Dysfunction. Experts believe that psychological factors such as stress, anxiety, guilt, depression, low self-esteem, and fear of sexual failure produce 10 to 20 percent of erectile dysfunction cases. Men with a physical cause for erectile dysfunction frequently experience the same sort of psychological reactions—stress, anxiety, guilt, depression.

Performance anxiety occurs when a patient is stressed or anxious; erections may be difficult or impossible. Stress increases the body's production of catecholamines, such as adrenaline and nor-adrenaline, which are specific rection inhibitors. Inconsistency in achieving long-lasting erections may increase stress, thus perpetuating a cycle resulting in the inability to achieve long-lasting erections.

Depression is another cause of psychogenic erectile dysfunction. Unfortunately, most anti-depressant medications themselves have the potential side effect of erectile dysfunction, which is not therapeutic for a depressed man. Techniques that will provide usable erections are often of great value in such instances. Current treatment practices include the use of psychotherapy, a vacuum constriction device, oral or self-injection therapy, or the insertion of a penile prosthesis.

Hormone-Induced Erectile Dysfunction. Endocrine-related hormonal abnormalities such as increased prolactin, steroid abuse by body-builders, too much or too little thyroid hormone, and hormones administered for prostate cancer may produce erectile dysfunction. Rarely is low testosterone alone responsible for poor erections. Testosterone stimulates desire, but is believed to have little effect on erections. In less than 5% of men with erectile dysfunction, the cause is an imbalance in certain hormones, such as testosterone, prolactin, or thyroid hormone.

Miscellaneous Causes. Other possible causes of erectile dysfunction include smoking, which affects blood flow in veins and arteries. Peyronie's disease produces scarring inside the penis and may be associated with a bend or curvature of the penis during an erection. Injuries also can produce scarring or bending of the penis and erectile dysfunction.

C. Diagnosis of Erectile Dysfunction. The diagnosis of erectile dysfunction may be understood as the presence of a condition limiting choices for sexual interaction and possibly limiting opportunity for sexual satisfaction. The impact of this condition depends very much on the dynamics of the relationship of the individual and his sexual partner and their expectation of performance. When changes in sexual function are perceived by the individual and his partner as a natural consequence of the aging process, they may modify their sexual behavior to accommodate the condition and maintain sexual satisfaction. Increasingly, men do not perceive erectile dysfunction as a normal part of aging and seek to identify means by which they may return to their previous level and range of sexual activities. Such levels and expectations and desires for future sexual interactions are important aspects of the evaluation of patients presenting with a chief complaint of erectile dysfunction.

In men of all ages, erectile failure may diminish willingness to initiate sexual relationships because of fear of inadequate sexual performance or rejection. Because males, especially older males, are particularly sensitive to the social support of intimate relationships, withdrawal from these relationships because of such fears may have a negative effect on their overall health.

Patient History. Medical and sexual histories help define the degree and nature of erectile dysfunction. A medical history can disclose diseases that lead to erectile dysfunction, while a simple recounting of sexual activity might distinguish among problems with sexual desire, erection, ejaculation, or orgasm.

Using certain prescription or illegal drugs can suggest a chemical cause, since drug effects account for 25 percent of erectile dysfunction cases. Cutting back on or substituting certain medications can often alleviate the problem.

Physical Examination. A physical examination can give clues to systemic problems. For example, if the penis is not sensitive to touching, a problem in the nervous system may be the cause. Abnormal secondary sex characteristics, such as hair pattern or breast enlargement, can point to hormonal problems, which would mean that the endocrine system is involved. The examiner might discover a circulatory problem by observing decreased pulses in the wrist or ankles. And unusual characteristics of the penis itself could suggest the source of the problem—for example, a penis that bends or curves when erect could be the result of Peyronie's disease.

Laboratory Tests. Several laboratory tests can help diagnose erectile dysfunction. Tests for systemic diseases include blood counts, urinalysis, lipid profile, and measurements of creatinine and liver enzymes. Measuring the amount of free testosterone in the blood can yield information about problems with the endocrine system and is indicated especially in patients with decreased sexual desire.

Other Tests. Monitoring erections that occur during sleep (nocturnal penile tumescence) can help rule out certain psychological causes of erectile dysfunction. Healthy men have involuntary erections during sleep. If nocturnal erections do not occur, then erectile dysfunction is likely to have a physical rather than psychological cause.

Psychosocial Examination. A psychosocial examination, using an interview and a questionnaire, reveals psychological factors. A man's sexual partner may also be interviewed to determine expectations and perceptions during sexual intercourse.

D. Prior-art Treatments of erectile dysfunction. Erectile dysfunction can be treated to a limited degree with a variety of methods. Cutting back on drugs with harmful side effects is considered first. For example, different drugs for high blood pressure work in different ways. Psychotherapy and behavior modifications in selected patients are considered next if indicated, followed by oral or locally injected drugs, vacuum devices, and surgically implanted devices. Surgery involving veins or arteries may also be considered.

Psychotherapy can help relieve anxiety when erectile dysfunction from physical causes is being treated, but is otherwise limited to treating only those causes which are truly psychological and not physical.

Drugs for treating erectile dysfunction can be taken orally, injected directly into the penis, or inserted into the urethra at the tip of the penis. While oral medicines such as Viagra, Levitra, and Cialis improve the response to sexual stimulation, they do have potential side effects and other limitations. Further, men who take nitrate-based drugs, such as nitroglycerin for heart problems, should not use any of these medications because the combination can produce a sudden drop in blood pressure. Taken before sexual activity, Viagra, Levitra and Cialis work by enhancing the effects of nitric oxide, a chemical that relaxes smooth muscles in the penis during sexual stimulation and allows increased blood flow. While oral medicines improve the response to sexual stimulation they do have potential side effects and other limitations, such as delayed time of onset. Further, men who take nitrate-based drugs, such as nitroglycerin for heart problems, should not use any of these medications because the combination can produce a sudden drop in blood pressure. In addition, none of these medications should be taken with any of the drugs called alpha-blockers, which are used to treat prostate enlargement or high blood pressure. Oral testosterone can reduce erectile dysfunction in some men with low levels of natural testosterone, but it is often ineffective and may produce liver damage. Injected drugs such as papaverine hydrochloride, phentolamine, and alprostadil widen blood vessels, but injections are inconvenient and such drugs may create unwanted side effects, including persistent erection and scarring. Insertion of a pellet of alprostadil into the urethra may produce aching in the penis, testicles, and area between the penis and rectum; warmth or burning sensation in the urethra; redness from increased blood flow to the penis; and minor urethral bleeding or spotting.

Mechanical vacuum/constriction devices produce erection by creating a partial vacuum around the penis, which draws blood into the penile corpora cavernosa, engorging and expanding the penis. Vacuum/constriction devices are at times effective at generating and maintaining erections in some patients with erectile dysfunction, but, as with intracavernosal injection therapy, there is a significant rate of patient dropout with these devices: the devices are difficult for many patients to use, and this is especially so in those with impaired manual dexterity. Also, vacuum/constriction devices may impair ejaculation, which then produces patient discomfort. Patients and their partners often are bothered by the lack of spontaneity in sexual relations that may occur with this procedure. The patient is at times also bothered by the general discomfort that can occur while using vacuum/constriction devices. Further complicating their use, partner involvement in training with vacuum/constriction devices is often important for successful outcome, especially in regard to establishing a mutually satisfying level of sexual activity.

Surgery to reconstruct arteries to increase flow of blood to the penis is almost never successful in older men with widespread arterial blockage. Surgery to block off veins that allow blood to leak from the penile tissues has questionable long-term effectiveness, and it is rarely used for that reason. Surgery to implant penile prostheses can restore the ability to achieve erection in many men with erectile dysfunction, but have variable effectiveness, complications, and acceptability, with the main problems being mechanical failure, infection, and erosions. Silicone particle shedding has been reported, including migration to regional lymph nodes. There is also a risk of the need for reoperation with all mechanical devices. Although the inflatable prostheses may yield a more physiologically natural appearance, they have had a higher rate of failure requiring reoperation. Men with diabetes mellitus, spinal cord injuries, or urinary tract infections have an increased risk of prosthesis-associated infection. This form of treatment is considered to be inappropriate in patients with severe penile corporal fibrosis, or severe medical illness. Circumcision may also be required for patients with phimosis and balanitis.

Thus, each of the prior art devices and methods has significant drawbacks, and there is a great need for novel and improved devices and methods for promoting or enhancing male erectile function, and for treating erectile dysfunction, particularly for comparatively simple, inexpensive, and non-invasive devices and methods of first resort which can be used by persons suffering from erectile dysfunction.

The inventive subject matter satisfies this need by providing novel, simple, and effective devices and methods for promoting or enhancing male erectile function, and for treating erectile dysfunction. Further, the inventive subject matter provides devices and methods for promoting or enhancing erectile function, including specifically those men who have no perceived or diagnosed erectile dysfunction, yet wish to have firmer, longer-lasting erections more often or more consistently.

Inventive Devices

Thus, the inventive subject matter relates to a device for external placement on the shaft of a user's penis, for promoting or enhancing male erectile function, comprising:

(i) a closed, hollow tube of relatively elastic material forming a ring (10), said hollow tube completely encircling the shaft of a user's penis when placed on said user's penis, or completely encircling the shaft of said user's penis and said user's scrotum and testicles; and (ii) a filled arch segment (12) within said hollow tube, for providing compression of a dorsal vein of said user's penis.

In another aspect of the inventive subject matter, the inventive device further comprises one or more additional hollow tube(s) for encircling the shaft of said user's penis, each said additional hollow tube forming a ring (20).

In a preferred embodiment, each said hollow tube has a filled arch segment (12) within said hollow tube.

In a more preferred embodiment, said hollow tubes are connected together over at least a portion of the circumference of the rings.

In another aspect of the inventive subject matter, each said ring (10 and 20) has an interior diameter which is the same as the other ring(s).

In another aspect of the inventive subject matter, at least one ring has an interior diameter which is different than the other ring(s).

In another aspect of the inventive subject matter, said rings are connected together over at least a portion of the circumference of the rings.

In one embodiment of the inventive subject matter in which said rings are connected together, each said ring (10 and 20) has an interior diameter which is the same as the other ring(s).

In one aspect of the inventive subject matter, the inventive device comprises a first ring (10) and a second ring (20).

In a preferred embodiment, said first ring (10) has an inner surface for contacting said penile shaft (14) and an outer surface distal to said penile shaft (16); and said second ring (20) is connected to the outer surface (16) of said first ring (10).

In another aspect of the inventive subject matter, the inventive device comprises a first ring (10) and a second ring (20), and further comprises one or more additional ring(s).

In a preferred embodiment, said first ring (10) has an inner surface for contacting said penile shaft (14) and an outer surface distal to said penile shaft (16); said second ring (20) is connected to the outer surface of said first ring (10); and said one or more additional ring(s) is/are connected to the outer surface of said first ring (10), to said second ring (20), to both the outer surface of said first ring (10) and to said second ring (20), or to one or more of said additional ring(s).

In another aspect of the inventive subject matter, at least one ring has an interior diameter which is different than the other ring(s).

In a preferred embodiment, the inventive device comprises a first ring (20), of larger interior diameter, and a second ring (10), of smaller interior diameter.

In a more preferred embodiment, said second ring (10) has an inner surface for contacting said penile shaft (14) and an outer surface distal to said penile shaft (16); and said first ring (20) is connected to the outer surface of said second ring (10).

In another aspect of the inventive subject matter, the inventive device further comprises one or more additional ring(s) (30).

In a preferred embodiment, said second ring (10) has an inner surface for contacting said penile shaft (14) and an outer surface distal to said penile shaft (16); said first ring (20) is connected to the outer surface of said second ring (10); and said one or more additional ring(s) (30) is/are connected to the outer surface of said second ring (10), to said first ring (20), to both the outer surface of said second ring (10) and to said first ring (20), or to one or more of said additional ring(s).

In an alternate aspect of the inventive subject matter, said relatively elastic material is selected from the group consisting of rubber, silicone, natural latex, and synthetic latex. Other relatively elastic materials, known to those of ordinary skill in the art, are also contemplated as within the inventive subject matter.

In another aspect of the inventive subject matter, said hollow tube is perforated. Perforation of the inventive devices permits release of air pressure within the hollow tubing, resulting in partial or complete flattening of the tubing over the non-filled portions. Perforating the tubing, with resulting flattening of the tubing, results in a small decrease in the pressure exerted by the inventive devices, and thereby permits the user to fine-tune the fit of the device.

In another aspect of the inventive subject matter, the inventive device additionally comprises an integral condom for application over the shaft of said user's penis. As is well known to one of ordinary skill in the art, a condom comprises a continuous elastic tubular wall (40) including a closed distal end (41) and an open proximal end (42). Further, condoms having such features as a reservoir tip (43), or incorporating lubricants, spermicide, and/or other active pharmaceutical agents, are also well known. The inventive devices incorporate a condom wherein the open proximal end (42) of said condom is attached to, or integrally formed with, a hollow tube forming a ring (10) of the inventive device. In adding an integral condom, the device so modified will serve the purposes of promoting or enhancing male erectile function, protecting the user and his partner from sexually transmitted diseases, and reducing or eliminating the risk of unwanted pregnancy.

In a preferred embodiment, said condom is selected from the group consisting of a ribbed condom, a ridged condom, a condom having raised knobs or other protrusions, a textured condom, and a lubricated condom,
  wherein said lubricated condom has lubrication on its outside surface, its inside surface, or both its inside surface and its outside surface.

Such texturing is incidental to the utility of the inventive devices, so long as such texturing does not interfere with the functions of protecting the user and his partner from sexually transmitted diseases, and reducing or eliminating the risk of unwanted pregnancy. It is known to one of ordinary skill in the art that an almost infinite variety of sizes, spacings, orientations, and patterns of ribs, ridges, raised knobs or other protrusions, and other texturing can be incorporated into the design and manufacture of condoms. Any pattern or combination of patterns of such texturing is contemplated to be within the scope of the inventive subject matter.

When combining an inventive device with a condom, the pressure that the ring (10) creates allows the user, or the manufacturer, to put a lubricant, preferably a relatively high density lubricant such as petroleum jelly, into the condom. A high density lubricant tends to remain trapped inside the condom as a result of such pressure, which effectively creates a partial seal at the base of the condom.

Incorporation of a lubricant into an inventive device allows a user to masturbate himself, or for someone else to masturbate him, and because the lubricant stays in place, lubrication remains relatively constant, except for a minor amount of initial absorption. The benefits of such a combination are superior lubrication, no greasy mess on the hands of the user or the user's partner, confinement of ejaculate, a convenient means of exciting the user prior to intercourse and, of course, use for intercourse.

It is further contemplated that an inventive combination device, incorporating a condom, optionally may include a multiple-layer condom, for example a double-layer condom, attached to a ring (10). Such an embodiment optionally includes lubricant inserted between the condom layers, and thus allows for lubricated penile stimulation without creating a greasy mess on the user's penis or the hands of the user and or the user's partner.

Further, such an arrangement is expected to provide significant advantages for a user's partner who does not produce sufficient lubrication; penile movement within the condom would feel essentially the same as regular intercourse to the user, while reducing the friction of the user's penis against an orifice of the user's partner.

In addition, if enough lubricant is put inside the condom, it actually increases the effective size of the penis without surgery or other enhancement techniques or drugs.

Extra lubricant within the condom can also be squeezed forward to the tip of the penis and then used in a very exciting manner to manually stimulate the female's clitoris.

In a more preferred embodiment, the open proximal end (42) of said condom is a discontinuous periphery having a sheath wall (40) that communicates with a hollow tube forming a ring (10) at its edge, and said periphery becomes discontinuous at a hole which is located within the sheath wall along said hollow tube forming a ring, through which the user's scrotum and testicles can protrude outside of the condom, as depicted generally in U.S. Pat. No. 5,111,831, the contents of which are hereby incorporated by reference in their entirety.

In another aspect of the inventive subject matter, the inventive device further comprises one or more additional hollow tube(s), each said hollow tube forming a ring, wherein at least one of said rings is sized for encircling both the shaft of said user's penis and said user's scrotum and testicles (200). As distinguished from the embodiments described above, the presently-described embodiment requires that at least one ring is sized for encircling both the shaft of said user's penis and said user's scrotum and testicles (200).

In a preferred embodiment, said rings are connected together over at least a portion of the circumference of the rings.

In a more preferred embodiment, the inventive device comprises a first ring (10), sized for encircling the shaft of said user's penis, and a second ring, sized for encircling both the shaft of said user's penis and said user's scrotum and testicles (200).

In another preferred embodiment, said first ring (10) has an inner surface proximal to said penile shaft (14) and an outer surface distal to said penile shaft (16), and
  wherein said second ring is connected to said outer surface of said first ring (10).

In another preferred embodiment, the inventive device further comprises one or more additional ring(s).

In a further preferred embodiment, said one or more additional ring(s) is/are connected to the outer surface of said first ring (10), to said second ring, to both the outer surface of said first ring (10) and to said second ring, or to one or more of said additional ring(s).

The inventive subject matter further relates to a device for external placement on the shaft of a user's penis, for promoting or enhancing male erectile function, comprising:

(i) a first closed, hollow tube of relatively elastic material forming a ring (10), said hollow tube completely encircling the shaft of a user's penis when placed on said user's penis; and (ii) a second closed, hollow tube of relatively elastic material forming a ring (20), said hollow tube completely encircling the shaft of a user's penis when placed on said user's penis, or completely encircling the shaft of said user's penis and said user's scrotum and testicles, wherein said first ring (10) has an inner surface proximal to said penile shaft (14) and an outer surface distal to said penile shaft (16), and wherein said second ring (20) is connected to said outer surface of said first ring (10).

In another aspect of the inventive subject matter, said first ring has an interior diameter which is the same as said second ring.

In another aspect of the inventive subject matter, the inventive device further comprises one or more additional ring(s).

In a preferred embodiment, said one or more additional ring(s) is/are connected to the outer surface of said first ring (10), to said second ring (20), to both the outer surface of said first ring (10) and to said second ring (20), or to one or more of said additional ring(s).

In another aspect of the inventive subject matter, said first ring has an interior diameter which is larger than said second ring.

In a preferred embodiment, the inventive device further comprises one or more additional ring(s).

In another preferred embodiment, said one or more additional ring(s) is/are connected to the outer surface of said second ring (10), to said first ring (20), to both the outer surface of said second ring (10) and to said first ring (20), or to one or more of said additional ring(s).

In another aspect of the inventive subject matter, said relatively elastic material is selected from the group consisting of rubber, silicone, natural latex, and synthetic latex.

In another aspect of the inventive subject matter, one or more of said hollow tube(s) is/are perforated.

In another aspect of the inventive subject matter, the inventive device additionally comprises an integral condom for application over the shaft of said user's penis, said condom comprising a continuous elastic tubular wall (40) including a closed distal end (41) and an open proximal end (42), wherein said open proximal end (42) of said condom is attached to, or integrally formed with, said first hollow tube forming a ring (10) or said second hollow tube forming a ring (20).

In a preferred embodiment, said condom is selected from the group consisting of a ribbed condom, a ridged condom, a condom having raised knobs or other protrusions, a textured condom, and a lubricated condom, wherein said lubricated condom has lubrication on its outside surface, its inside surface, or both its inside surface and its outside surface.

In another preferred embodiment, the open proximal end of said condom is a discontinuous periphery having a sheath wall that communicates with said second hollow tube at its edge, and said periphery becomes discontinuous at a hole which is located within the sheath wall along said second hollow tube, through which the user's scrotum and testicles can protrude outside of the condom.

Inventive Methods

In addition, the inventive subject matter relates to a method for promoting or enhancing male erectile function, comprising:

(a) providing a device for providing compression of a dorsal vein of a user's penis which is sufficient to promote arterial blood inflow in excess of venous blood outflow from said user's penis, comprising:

(i) a first closed, hollow tube of relatively elastic material forming a first ring (10), said hollow tube completely encircling the shaft of said user's penis when placed on said user's penis, or completely encircling the shaft of said user's penis and said user's scrotum and testicles, and (ii) a filled arch segment (12) within said hollow tube; and (b) placing said device so as to encircle said user's penis with said filled arch segment (12) located on the dorsal surface of said user's penis.

In a preferred embodiment, said device is placed so as to encircle the base of said user's penis.

In another aspect of the inventive subject matter, said device further comprises a second hollow tube for encircling the shaft of said user's penis, said additional hollow tube forming a second ring (20), and wherein said device optionally comprises one or more additional hollow tube(s), and wherein each said additional hollow tube forms an additional ring.

In another aspect of the inventive subject matter, each said hollow tube has a filled arch segment (12) within said hollow tube.

In another aspect of the inventive subject matter, at least one ring has an interior diameter which is different than the other ring(s), and wherein a ring having the largest interior diameter is placed most proximal to said user's torso.

In another aspect of the inventive subject matter, at least one ring has an interior diameter which is different than the other ring(s), and wherein a ring having the smallest interior diameter is placed most distal to said user's torso.

In a preferred embodiment, at least one ring has an interior diameter which is different than the other ring(s), and a ring having the largest interior diameter is placed most proximal to said user's torso and a ring having the smallest interior diameter is placed most distal to said user's torso.

In a preferred embodiment, said rings are connected together over at least a portion of the circumference of the rings.

In another aspect of the inventive subject matter, said device is placed so as to encircle the base of said user's penis, said largest ring is placed most proximal to said user's torso and said smallest ring is placed most distal to said user's torso.

In another aspect of the inventive subject matter, the inventive method comprises a device which further comprises one or more additional hollow tube(s), each said hollow tube forming a ring, wherein at least one of said one or more additional ring(s) has an interior diameter which is different than the other ring(s), and is sized for encircling both the shaft of said user's penis and said user's scrotum and testicles (200).

In a preferred embodiment, each said hollow tube has a filled arch segment (12) within said hollow tube.

In another preferred embodiment, a ring having the largest interior diameter is placed most proximal to said user's torso and encircles said user's scrotum, testicles, and penis.

In another preferred embodiment, a ring having the smallest interior diameter is placed most distal to said user's torso and encircles said user's penis.

In a more preferred embodiment, a ring having the largest interior diameter is placed most proximal to said user's torso and encircles said user's scrotum, testicles, and penis, and a ring having the smallest interior diameter is placed most distal to said user's torso and encircles said user's penis.

In another aspect of the inventive subject matter, the inventive device further comprises one or more additional ring(s) distal to said ring having the smallest interior diameter.

In another aspect of the inventive subject matter, said rings are connected together over at least a portion of the circumference of the rings.

In another aspect of the inventive subject matter, when said device is placed so as to encircle the base of said user's penis and said user's scrotum and testicles, said ring for encircling both the shaft of said user's penis and said user's scrotum and testicles is placed most proximal to said user's torso, and said ring for encircling the shaft of said user's penis is placed most distal to said user's torso.

In another aspect of the inventive subject matter, the inventive device further comprises one or more additional ring(s) distal to said ring for encircling the shaft of said user's penis.

Further, the inventive subject matter relates to a method for promoting or enhancing male erectile function and promoting responsible sexual practices, comprising:

(a) applying a condom, having a closed distal end (41) and an open proximal end (42), to said user's penis;

(b) providing a device comprising:

(i) a closed, hollow tube of relatively elastic material forming a ring, said hollow tube completely encircling the shaft of a user's penis when placed on said user's penis, or completely encircling the shaft of said user's penis and said user's scrotum and testicles, and (ii) a filled arch segment (12) within said hollow tube; and (c) placing said device so as to encircle the base of said user's penis and entrap the open proximal end (42) of said condom, with said filled arch segment (12) located on the dorsal surface of said user's penis.

In a preferred embodiment, said ring is integrally formed with or attached to said condom, said condom comprising a continuous elastic tubular wall (40) including a closed distal end (41) and an open proximal end (42), wherein said open proximal end (42) of said condom is attached to, or integrally formed with, said hollow tube forming a ring.

Additionally, the inventive subject matter relates to a method for treating erectile dysfunction in a patient in need thereof, comprising:

(a) providing a device for providing compression of a dorsal vein of a user's penis which is sufficient to promote arterial blood inflow in excess of venous blood outflow from said user's penis, comprising:

(i) a first closed, hollow tube of relatively elastic material forming a first ring (10), said hollow tube completely encircling the shaft of said user's penis when placed on said user's penis, or completely encircling the shaft of said user's penis and said user's scrotum and testicles, and (ii) a filled arch segment (12) within said hollow tube; and (b) placing said device so as to encircle said user's penis with said filled arch segment (12) located on the dorsal surface of said user's penis.

It will be understood by one of ordinary skill in the art that the inventive devices for promoting or enhancing male erectile function, as described herein, may be packaged in a kit having a range of sizes of single rings, double rings, and/or triple rings, and preferably in a kit having a combination of single rings of different sizes, double rings of different sizes, and/or triple rings of different sizes.

It will be further understood by one of ordinary skill in the art that an inventive device for promoting or enhancing male erectile function, as described herein, may be packaged in a kit comprising:

(a) a double ring, (b) a triple ring, and (c) a plurality of single rings of different sizes.

In a preferred embodiment, an inventive kit additionally comprises at least one condom, and preferably a plurality of condoms, wherein said condom(s) is/are selected from the group consisting of a ribbed condom, a ridged condom, a condom having raised knobs or other protrusions, a textured condom, and a mixed selection thereof.

It is anticipated, although not required, that an inventive devices and the inventive kits, as described herein, will also include instructions for use of the inventive devices, and/or instructions for accomplishing the inventive methods.

EXAMPLES

The following examples are illustrative of the present inventive subject matter and are not intended to be limitations thereon.

Example 1

Treatment of Erectile Dysfunction: Clinical Results

The following example illustrates a method for treating erectile dysfunction in a male human in need thereof, utilizing a device provided according to the present inventive subject matter.

The male erectile response is a vascular event initiated by neuronal action and maintained by a complex interplay between vascular and neurological events. In its most common form, it is initiated by a central nervous system event that integrates psychogenic stimuli, such as perception, desire, etc., and controls the sympathetic and parasympathetic enervation of the penis. Sensory stimuli from the penis are important in continuing this process and in initiating a reflex arc that may produce erection under proper circumstances and may help to maintain erection during sexual activity.

Parasympathetic input allows erection by relaxation of trabecular smooth muscle and dilation of the helicine arteries of the penis. This leads to expansion of the lacunar spaces and entrapment of blood by compressing venules against the tunica albuginea, a process referred to as the corporal venoocclusive mechanism. The tunica albuginea must have sufficient stiffness to compress the venules penetrating it so that venous outflow is blocked and sufficient tumescence and rigidity can occur.

Acetylcholine released by the parasympathetic nerves is thought to act primarily on endothelial cells to release a second nonadrenergic-noncholinergic carrier of the signal that relaxes the trabecular smooth muscle. Nitric oxide released by the endothelial cells, and possibly also of neural origin, is currently thought to be the leading of several candidates as this nonadrenergic-noncholinergic transmitter; but this has not yet been conclusively demonstrated to the exclusion of other potentially important substances, e.g., vasoactive intestinal polypeptide. The relaxing effect of nitric oxide on the trabecular smooth muscle may be mediated through its stimulation of guanylate cyclase and the production of cyclic guanosine monophosphate, which would then function as a second messenger in this system.

Constriction of the trabecular smooth muscle and helicine arteries induced by sympathetic enervation makes the penis flaccid, with blood pressure in the cavernosal sinuses of the penis near venous pressure. Acetylcholine is thought to decrease sympathetic tone. This may be important in a permissive sense for adequate trabecular smooth muscle relaxation and consequent effective action of other mediators in achieving sufficient inflow of blood into the lacunar spaces. When the trabecular smooth muscle relaxes and helicine arteries dilate in response to parasympathetic stimulation and decreased sympathetic tone, increased blood flow fills the cavernous spaces, increasing the pressure within these spaces so that the penis becomes erect. As the venules are compressed against the tunica albuginea, penile pressure approaches arterial pressure, causing rigidity. Once this state is achieved, arterial inflow is reduced to a level that matches venous outflow.

Because adequate arterial supply is critical for erection, any disorder that impairs blood flow may be implicated in the etiology of erectile failure. Most of the medical disorders associated with erectile dysfunction appear to affect the arterial system. Some disorders may interfere with the corporal veno-occlusive mechanism and result in failure to trap blood within the penis, or produce leakage such that an erection cannot be maintained or is easily lost.

In light of the physiology and psychology of male erectile functioning, Applicant has tested the inventive devices in his clinical practice, and is achieving very dramatic results. Patients with erectile dysfunction have reported dramatic results. Typical reports include men who could not even maintain an erection long enough to have intercourse for longer than a few minutes being able to "make love as long as I want to-up to an hour" or reports of "the best love-making since I first got married 30 years ago", etc.

In addition to patients with erectile dysfunction, the results Applicant has achieved with "normal" males is quite remarkable. One normally functioning 45 year old male who would have usually been able to have intercourse about three times per week and rarely more than once a day reported having twenty one orgasms in three days. Another "normal" 54 year old male who very rarely experienced more than one orgasm in a single day reported having six orgasms in an hour and fifty minutes.

Example 2

A Method for Promoting or Enhancing Male Erectile Function

The following example illustrates a method for promoting or enhancing male erectile function in a male human, utilizing a kit comprising devices according to the present inventive subject matter.

Initially, oral and written interviews are conducted with candidates for prescription of the inventive devices and methods. Those who continue as patients are provided with a kit having a number of rubber rings in varying sizes, and some rings that are connected to others to create both two and three-ring devices. In this example, each ring is reinforced on one side with an arch of hard rubber. This side is to be worn on top of the penis, which creates a differential in the amount of pressure that is applied over the dorsal aspect of the penis compared to the ventral or lateral aspects. It is this particular element of the ring design that makes them particularly effective.

The simplest use of the inventive methods can be accomplished by taking one of the smaller rings and slipping it over the shaft of the patient's penis, with the stiff, reinforced edge on top, and then pulling it up to a position where it is as snug as possible against the base of the penis. The ring size that the patient uses should be determined by the diameter of the penis. To start with, the patient should choose a size that is snug but can be slipped easily over the penis in a flaccid state. They can then familiarize themselves with the device's effect by masturbating or simply proceed with lovemaking.

Generally, smaller sizes will be more effective and larger sizes will be more comfortable. The patient may need to find his own balance between comfort and effectiveness.

The following are some other combinations of rings that the patient may want to try:

A. Keep the first ring in place and slip a second smaller ring over the shaft of the penis, also with stiff edge on top, and pull it to a position where it is as snug as possible against the first ring. Then pull the first ring up more snugly against the base of the penis and again pull the second ring up as close as possible next to the first ring.

B. Keep the first and second ring in place. Utilize a single larger ring ("body ring") and slip it over both the penis and scrotum so that it comes to rest against the body, stiff edge up.

C. Remove the previous rings. Use a double ring by stretching the largest ring ("anchor ring") and slip it over the scrotum and then the penis, stiff side up; then slip the smaller ring over the shaft of the penis and pull it up firmly against the base of the penis. Pull both rings back toward the body as far as possible.

D. Remove any previous rings and use the triple ring. Stretch the large anchor ring, stiff side up, and slip it over the scrotum and then the penis; then slip the other two rings over the shaft of the penis and pull them snugly against the base of the penis.

E. Utilize the set-up described in D, but add one of the smaller rings by slipping it, stiff side up, over the shaft of the penis and pull it firmly against the outer-most ring of the triple ring.

F. Utilize the set-up described in E, but add a second smaller ring by slipping it onto the shaft of the penis, and then pull it snugly against the outer-most ring.

Using any of these set-ups, the patient may wish to reposition the rings, after erection has begun, by pulling any of the shaft rings back against the base of the penis or pulling any anchor rings or body rings back as far as possible toward the body.

An additional technique that can be combined with any of these ring combinations involves using the patient's built-in "penis pump". The penis is actually much larger than the part that extends out from the body. The internal hidden portion can be identified when the patient is sexually excited by pressing upward with fingertips into the pelvic area just behind the scrotum. In this manner the engorged "hidden chamber" can be quite easily felt.

When rings are being worn, a slight "back pressure" is created so that engorgement of this internal chamber begins to occur before erection of the penis. In the initial stage of sexual excitement the blood that begins accumulating in this chamber can be "milked" forward into the external penis with the fingertips. This is accomplished by pressing gently with the fingertips, beginning about an inch in front of the anus, and pulling them forward to the scrotum. As the patient does this, he will "milk" the blood from the internal chamber through the constriction ring (s) and into the external penis, where it will tend to remain because of the ring constriction. If the patient is wearing only (a) shaft ring(s), with no body ring or anchor ring behind the scrotum, he can extend the milking action through the scrotum, between the testicles, up to the inside edge of the innermost shaft ring.

By using this technique, at least a small amount of blood can be milked into the penis, and it should be noted that with even the slightest increase in tumescence penile sensitivity increases substantially. Therefore, if penile stimulation is done in alternation with this technique it becomes increasingly effective, at least up to a certain point.

Example 3

A Method for Enhancing Male Erectile Function and Female Pleasure

The following example illustrates a method for enhancing human male erectile function and enhancing female sexual partner pleasure, utilizing devices according to the present inventive subject matter. It is expected that there are no firm boundaries limiting use of the inventive devices and methods to "normal" or "dysfunctional" men. Thus, this example is not considered to be limiting of the inventive subject matter, but merely illustrative. However, this embodiment may more preferably be used by "normally functioning" men, since a patient with erectile dysfunction may have more difficulty achieving an initial erection.

Once a man's initial erection has been achieved, this embodiment augments sexual functioning as explained below. It involves using a much larger number of rings on the shaft of the penis than in other examples discussed herein. This particular approach can be accomplished in at least two ways:

1. A device combination of a double ring with the larger ring worn over the penis and scrotum; and the second ring over the penile shaft; and five to seven single rings, ranging from medium to small sizes, with the medium sizes at proximal end of the penile shaft with progressively smaller sizes toward the distal end. The rings, as always, should be arranged as close to the base of the penis as possible. In this case the rings cover most of the penis but, when erect, leave about two to three inches uncovered at the distal end.

2. Alternately, a device combination of one large body ring and an additional one or two slightly smaller body rings placed over both the scrotum and penis; and between five and seven medium to small rings over the proximal end of the shaft of the penis.

The results from these combinations have provided enhancement of the sexual experience for both male and female partners. The larger number of rings substantially enhances male erections. Even after achieving an orgasm, with the support of the rings the male may remain in a semi-erect state. Then, after a very short refractory period, he may discover that by using the "penis pump" technique, he can quickly regain a fully erect state. The male may also be able to regain rigidity by squeezing the muscles around the "hidden chamber" of the penis, as described above, by tensing muscles that surround that area. These muscles are the same that would be used to stop the flow of the urine stream. This effect can also be accomplished by tensing the muscles of the buttocks.

This embodiment also has the potential of directly enhancing the sexual experience for female partners. In this embodiment the rings extend up the shaft of the penis for a much greater distance than in other embodiments. The additional rings both widen the penis in this area and give the penis an altered, textured—soft, pliable, semicircles—surface for added stimulation of both the outer two inches of the vaginal entrance, and at certain angles, direct stimulation of the clitoris.

In this regard, it should be noted that there are some analogous vascular properties between the penis and the vaginal lips and clitoris. As discussed above, blood can be massaged into the "external" penis by "milking" blood from the internal chamber, which is located between the scrotum and anus. In a similar fashion, vascular engorgement of the clitoris, which increases sensitivity and therefore sexual response, can be hastened during sexual stimulation by "milking" blood flow in the genital area. This can be accomplished by gently pressing with fingertips, on either side of the vaginal opening, up over the labia majora toward the clitoris. Likewise, the added pressure exerted over this same area by the extra rings around the base of the penis, tends to push or "milk" additional blood upward toward the clitoris. The resultant effect of this is increased female excitation and orgasmic pleasure. With some awareness on the part of the male sexual partner, penile pressure can be exerted in a manner that will maximize this effect. The female partner can also experience direct stimulation of the clitoris from these additional rings by adjusting her position and angle to maximize stimulation.

The inventive subject matter being thus described, it will be obvious that the same may be modified or varied in many ways. Such modifications and variations are not to be regarded as a departure from the spirit and scope of the inventive subject matter and all such modifications and variations are intended to be included within the scope of the following claims.

I claim:

1. A device for external placement on the shaft of a user's penis, for promoting or enhancing male erectile function, consisting of:
   (i) a closed, hollow tube of relatively elastic material forming a continuous ring, said hollow tube having a length that completely encircles the shaft of a user's penis when placed on said user's penis, or completely encircles the shaft of said user's penis and said user's scrotum and testicles, said hollow tube having a uniform outer diameter completely along the length of the continuous ring; and
   (ii) a hard-rubber arch-shaped segment filling a portion of said hollow tube, for providing compression of a dorsal vein of said user's penis, an outer diameter of the arch-shaped segment being of a smaller diameter than the outer diameter of the hollow tube.

2. The device of claim 1, further comprising one or more additional hollow tube(s) for encircling the shaft of said user's penis, each said additional hollow tube forming a ring.

3. The device of claim 2, wherein each said hollow tube has a filled arch segment within said hollow tube.

4. The device of claim 3, wherein said hollow tubes are connected together over at least a portion of the circumference of the rings.

5. The device of claim 2, wherein each said ring has an interior diameter which is the same as the other ring(s).

6. The device of claim 2, wherein at least one ring has an interior diameter which is different than the other ring(s).

7. The device of claim 2, wherein said rings are connected together over at least a portion of the circumference of the rings.

8. The device of claim 7, wherein each said ring has an interior diameter which is the same as the other ring(s).

9. The device of claim 8, comprising a first ring and a second ring.

10. The device of claim 9, wherein:
(a) said first ring has an inner surface for contacting said penile shaft and an outer surface distal to said penile shaft; and
(b) said second ring is connected to the outer surface of said first ring.

11. The device of claim 9, further comprising one or more additional ring(s).

12. The device of claim 11, wherein:
(a) said first ring has an inner surface for contacting said penile shaft and an outer surface distal to said penile shaft;
(b) said second ring is connected to the outer surface of said first ring; and
(c) said one or more additional ring(s) is/are connected to the outer surface of said first ring, to said second ring, to both the outer surface of said first ring and to said second ring, or to one or more of said additional ring(s).

13. The device of claim 7, wherein at least one ring has an interior diameter which is different than the other ring(s).

14. The device of claim 13, comprising a first ring, of larger interior diameter, and a second ring, of smaller interior diameter.

15. The device of claim 14, wherein:
(a) said second ring has an inner surface for contacting said penile shaft and an outer surface distal to said penile shaft; and
(b) said first ring is connected to the outer surface of said second ring.

16. The device of claim 14, further comprising one or more additional ring(s).

17. The device of claim 16, wherein:
(a) said second ring has an inner surface for contacting said penile shaft and an outer surface distal to said penile shaft;
(b) said first ring is connected to the outer surface of said second ring; and
(c) said one or more additional ring(s) is/are connected to the outer surface of said second ring, to said first ring, to both the outer surface of said second ring and to said first ring, or to one or more of said additional ring(s).

18. The device of claim 1, wherein said relatively elastic material is selected from the group consisting of rubber, silicone, natural latex, and synthetic latex.

19. The device of claim 1, wherein said hollow tube is perforated.

20. The device of claim 1, additionally comprising an integral condom for application over the shaft of said user's penis, said condom comprising a continuous elastic tubular wall including a closed distal end and an open proximal end,
wherein said open proximal end of said condom is attached to, or integrally formed with, said hollow tube forming a ring.

21. The device of claim 20, wherein said condom is selected from the group consisting of a ribbed condom, a ridged condom, a condom having raised knobs or other protrusions, a textured condom, and a lubricated condom,
wherein said lubricated condom has lubrication on its outside surface, its inside surface, or both its inside surface and its outside surface.

22. The device of claim 20, wherein the open proximal end of said condom is a discontinuous periphery having a sheath wall that communicates with a hollow tube forming a ring at its edge, and said periphery becomes discontinuous at a hole which is located within the sheath wall along said hollow tube forming a ring, through which the user's scrotum and testicles can protrude outside of the condom.

23. The device of claim 1, comprising one or more additional hollow tube(s), each said hollow tube forming a ring,
wherein at least one of said rings is sized for encircling both the shaft of said user's penis and said user's scrotum and testicles.

24. The device of claim 23, wherein said rings are connected together over at least a portion of the circumference of the rings.

25. The device of claim 24, comprising a first ring, sized for encircling the shaft of said user's penis, and a second ring, sized for encircling both the shaft of said user's penis and said user's scrotum and testicles.

26. The device of claim 25, wherein said first ring has an inner surface proximal to said penile shaft and an outer surface distal to said penile shaft, and
wherein said second ring is connected to said outer surface of said first ring.

27. The device of claim 26, further comprising one or more additional ring(s).

28. The device of claim 27, wherein said one or more additional ring(s) is/are connected to the outer surface of said first ring, to said second ring, to both the outer surface of said first ring and to said second ring, or to one or more of said additional ring(s).

29. A device for external placement on the shaft of a user's penis, for promoting or enhancing male erectile function, consisting of:
(i) a first closed, hollow tube of relatively elastic material forming a continuous ring, said hollow tube having a length that completely encircles the shaft of a user's penis when placed on said user's penis, said hollow tube having a uniform outer diameter completely along the length of the continuous ring; and
(ii) a second closed, hollow tube of relatively elastic material forming a ring, said hollow tube completely encircling the shaft of a user's penis when placed on said user's penis, or completely encircling the shaft of said user's penis and said user's scrotum and testicles,
wherein said first ring has an inner surface proximal to said penile shaft and an outer surface distal to said penile shaft, and
wherein said second ring is connected to said outer surface of said first ring, wherein at least one of the first and second closed hollow tubes contains a hard-rubber arch-shaped segment filling a portion of said hollow tube, for providing compression of a dorsal vein of said user's penis, an outer diameter of the arch-shaped segment being of a smaller diameter than the uniform outer diameter of the hollow tube containing the filled arch-shaped segment.

30. The device of claim 29, wherein said first ring has an interior diameter which is the same as said second ring.

31. The device of claim 30, further comprising one or more additional ring(s).

32. The device of claim 31, wherein said one or more additional ring(s) is/are connected to the outer surface of said first ring, to said second ring, to both the outer surface of said first ring and to said second ring, or to one or more of said additional ring(s).

33. The device of claim 29, wherein said first ring has an interior diameter which is larger than said second ring.

34. The device of claim 33, further comprising one or more additional ring(s).

35. The device of claim 34, wherein said one or more additional ring(s) is/are connected to the outer surface of said second ring, to said first ring, to both the outer surface of said second ring and to said first ring, or to one or more of said additional ring(s).

36. The device of claim 29, wherein said relatively elastic material is selected from the group consisting of rubber, silicone, natural latex, and synthetic latex.

37. The device of claim 29, wherein one or more of said hollow tube(s) is/are perforated.

38. The device of claim 29, additionally comprising an integral condom for application over the shaft of said user's penis, said condom comprising a continuous elastic tubular wall including a closed distal end and an open proximal end,
wherein said open proximal end of said condom is attached to, or integrally formed with, said first hollow tube forming a ring or said second hollow tube forming a ring.

39. The device of claim 38, wherein said condom is selected from the group consisting of a ribbed condom, a ridged condom, a condom having raised knobs or other protrusions, a textured condom, and a lubricated condom,
wherein said lubricated condom has lubrication on its outside surface, its inside surface, or both its inside surface and its outside surface.

40. The device of claim 38, wherein the open proximal end of said condom is a discontinuous periphery having a sheath wall that communicates with said second hollow tube at its edge, and said periphery becomes discontinuous at a hole which is located within the sheath wall along said second hollow tube, through which the user's scrotum and testicles can protrude outside of the condom.

41. A method for promoting or enhancing male erectile function, comprising:
(a) providing a device for providing compression of a dorsal vein of a user's penis which is sufficient to promote arterial blood inflow in excess of venous blood outflow from said user's penis, consisting of:
  (i) a first closed, hollow tube of relatively elastic material forming a first continuous ring, said hollow tube having a length that completely encircles the shaft of said user's penis when placed on said user's penis, or completely encircles the shaft of said user's penis and said user's scrotum and testicles, said hollow tube having a uniform outer diameter completely along the length of the continuous ring, and
  (ii) a hard-rubber arch-shaped segment filling a portion of said hollow tube, an outer diameter of the arch-shaped segment being of a smaller diameter than the uniform outer diameter of said hollow tube; and
(b) placing said device so as to encircle said user's penis with said filled arch segment located on the dorsal surface of said user's penis.

42. The method of claim 41, wherein said device is placed so as to encircle the base of said user's penis.

43. The method of claim 41, wherein said device further comprises a second hollow tube for encircling the shaft of said user's penis, said additional hollow tube forming a second ring, and wherein said device optionally comprises one or more additional hollow tube(s), and wherein each said additional hollow tube forms an additional ring.

44. The method of claim 43, wherein each said hollow tube has a filled arch segment within said hollow tube.

45. The method of claim 43, wherein at least one ring has an interior diameter which is different than the other ring(s), and wherein a ring having the largest interior diameter is placed most proximal to said user's torso.

46. The method of claim 43, wherein at least one ring has an interior diameter which is different than the other ring(s), and wherein a ring having the smallest interior diameter is placed most distal to said user's torso.

47. The method of claim 43, wherein at least one ring has an interior diameter which is different than the other ring(s), and a ring having the largest interior diameter is placed most proximal to said user's torso and a ring having the smallest interior diameter is placed most distal to said user's torso.

48. The method of claim 43, wherein said rings are connected together over at least a portion of the circumference of the rings.

49. The method of claim 43, wherein, when said device is placed so as to encircle the base of said user's penis, said largest ring is placed most proximal to said user's torso and said smallest ring is placed most distal to said user's torso.

50. The method of claim 41, comprising one or more additional hollow tube(s), each said hollow tube forming a ring,
wherein at least one of said one or more additional ring(s) has an interior diameter which is different than the other ring(s), and is sized for encircling both the shaft of said user's penis and said user's scrotum and testicles.

51. The method of claim 50, wherein each said hollow tube has a filled arch segment within said hollow tube.

52. The method of claim 50, wherein a ring having the largest interior diameter is placed most proximal to said user's torso and encircles said user's scrotum, testicles, and penis.

53. The method of claim 50, wherein a ring having the smallest interior diameter is placed most distal to said user's torso and encircles said user's penis.

54. The method of claim 50, wherein a ring having the largest interior diameter is placed most proximal to said user's torso and encircles said user's scrotum, testicles, and penis, and a ring having the smallest interior diameter is placed most distal to said user's torso and encircles said user's penis.

55. The method of claim 54, further comprising one or more additional ring(s) distal to said ring having the smallest interior diameter.

56. The method of claim 50, wherein said rings are connected together over at least a portion of the circumference of the rings.

57. The method of claim 50, wherein, when said device is placed so as to encircle the base of said user's penis and said user's scrotum and testicles, said ring for encircling both the shaft of said user's penis and said user's scrotum and testicles is placed most proximal to said user's torso, and said ring for encircling the shaft of said user's penis is placed most distal to said user's torso.

58. The method of claim 57, further comprising one or more additional ring(s) distal to said ring for encircling the shaft of said user's penis.

59. A method for promoting or enhancing male erectile function and promoting responsible sexual practices, comprising:
(a) applying a condom, having a closed distal end and an open proximal end, to said user's penis;
(b) providing a device consisting of:
  (i) a closed, hollow tube of relatively elastic material forming a continuous ring, said hollow tube having a length that completely encircles the shaft of a user's penis when placed on said user's penis, or completely encircles the shaft of said user's penis and said user's scrotum and testicles, said hollow tube having a uniform outer diameter completely along the length of the continuous ring, and
  (ii) a hard-rubber arch-shaped segment filling a portion of said hollow tube providing compression of the dorsal vein, an outer diameter of the arch-shaped segment being of a smaller diameter than the uniform outer diameter of the hollow tube; and (c) placing said device so as to encircle the base of said user's penis and entrap the open proximal end of said condom, with said filled arch segment located on the dorsal surface of said user's penis.

60. The method of claim 59, wherein said ring is integrally formed with or attached to said condom, said condom comprising a continuous elastic tubular wall including a closed distal end and an open proximal end, wherein said open proximal end of said condom is attached to, or integrally formed with, said hollow tube forming a ring.

61. A method for treating erectile dysfunction in a patient in need thereof, comprising:

(a) providing a device for providing compression of a dorsal vein of a user's penis which is sufficient to promote arterial blood inflow in excess of venous blood outflow from said user's penis, said device consisting of:

(i) a first closed, hollow tube of relatively elastic material forming a first continuous ring, said hollow tube having a length that completely encircles the shaft of said user's penis when placed on said user's penis, or completely encircles the shaft of said user's penis and said user's scrotum and testicles, and (ii) a hard-rubber arch-shaped segment filling a portion of said hollow tube, an outer diameter of the arch-shaped segment being of a smaller diameter than the uniform outer diameter of the hollow tube; and (b) placing said device so as to encircle said user's penis with said filled arch segment located on the dorsal surface of said user's penis.

\* \* \* \* \*